US00PP25311P3

(12) United States Plant Patent
de Boer

(10) Patent No.: US PP25,311 P3
(45) Date of Patent: Feb. 24, 2015

(54) ***NEPHROLEPIS* PLANT NAMED 'GREEN MOMENT'**

(50) Latin Name: *Nephrolepis exaltata*
Varietal Denomination: Green Moment

(76) Inventor: Petrus de Boer, Asten (NL)

( * ) Notice: Subject to any disclaimer, the term of this patent is extended or adjusted under 35 U.S.C. 154(b) by 146 days.

(21) Appl. No.: 13/507,702

(22) Filed: Jul. 20, 2012

(65) Prior Publication Data

US 2014/0026276 P1 Jan. 23, 2014

(51) Int. Cl.
*A01H 5/00* (2006.01)

(52) U.S. Cl.
USPC ..... Plt./379

(58) Field of Classification Search
USPC ..... Plt./379
See application file for complete search history.

*Primary Examiner* — Kent L Bell
(74) *Attorney, Agent, or Firm* — Cassandra Bright

(57) ABSTRACT

A new and distinct *Nephrolepis exaltata* cultivar named 'Green Moment' is disclosed, characterized by moderate to rapid growth medium, green foliage and unique frond abscission characteristics. The new variety is a *Nephrolepis exaltata*, typically produced as an indoor ornamental plant.

1 Drawing Sheet

Latin name of the genus and species: *Nephrolepis exaltata.*
Variety denomination: 'Green Moment'.

BACKGROUND OF THE INVENTION

The new cultivar is the product of chance discovery. The new variety originated as a naturally occurring mutation, whole plant mutation of the unpatented 'Boston Blue Bell' variety of *Nephrolepis exaltata.*

The new variety was discovered by the inventor, Petrus de Boer, a citizen of the Netherlands, during Spring 2006 in a commercial greenhouse belonging to the inventor in Asten, the Netherlands. After identifying the single plant as a potentially interesting selection, the inventor continued confidential testing of 'Green Moment' at his own greenhouse, assessing the stability of the unique characteristics of this variety.

Asexual reproduction of the new cultivar 'Green Moment' was first performed at a lab in Burgh-haamstede, the Netherlands, by tissue culture in May of 2011. Access to all plants was restricted, as plants were kept in restricted locations that are not open to the public. Through subsequent propagation by tissue culture, multiple generations have been reproduced, which have shown that the unique features of this cultivar are stable and reproduced true to type.

SUMMARY OF THE INVENTION

The cultivar 'Green Moment' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Green Moment'. These characteristics in combination distinguish 'Green Moment' as a new and distinct *Nephrolepis exaltata* cultivar:

1. Medium green colored fronds.
2. Attractive frond abscission behavior.

PARENT COMPARISON

Plants of the new cultivar 'Green Moment' are similar to the parent, *Nephrolepis exaltata* 'Boston Blue Bell' in most horticultural characteristics. The new variety, however, produces fronds that are green in color whereas 'Boston Blue Bell' produces fronds that are yellow-green. 'Green Moment' is taller than 'Boston Blue Bell' as well as faster growing. Fronds of 'Green Moment' have much less abscission, compared to 'Boston Blue Bell'. Pinnae of 'Green Moment' are bigger that those of 'Boston Blue Bell'.

COMMERCIAL COMPARISON

Plants of the new cultivar 'Green Moment' are also comparable to the commercial variety *Nephrolepis exaltata* 'Fluffy Ruffles', unpatented, in most horticultural characteristics. Plants of the new variety, produce darker green foliage arranged at a less acute angle, and with less undulation.

Plants of the new cultivar 'Green Moment' are also comparable to the commercial variety *Nephrolepis exaltata* 'Green Delight', filed concurrently, U.S. application Ser. No. 13/507,705, in most horticultural characteristics. Plants of 'Green Moment', however, grow more rapidly and produce darker green foliage, emerging at a less acute angle.

BRIEF DESCRIPTION OF THE PHOTOGRAPH

The accompanying photograph in FIG. 1 illustrates in full color a typical plant of 'Green Moment' grown in a commercial greenhouse in Asten, the Netherlands. This plant is approximately 22 weeks old, shown planted in a 17 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Green Moment' plants grown in a greenhouse in Asten, The Netherlands. This was done in June 2012 with a plant 22 weeks old, in a 17 cm. pot. Temperatures ranged from 18° C. at night to 20° C. during the day. No artificial light, photoperiodic treatments were given to the plants. No chemical treatments were given to plants. Measurements and numerical values represent averages of typical plant types.

Botanical classification: *Nephrolepis exaltata* 'Green Moment'.

PROPAGATION

Time to initiate roots: Approximately 21-28 days from a rooted plantlet at approximately 22° C.

Time to produce rooted plantlet: Approximately 5 weeks at approximately 22° C.

Root description: Very dense and freely branching, moderately fine, slightly fibrous, non-fleshy, coloured near RHS Brown 199D and N199B.

PLANT

Growth habit: Broad spreading-upright.

Plant shape: Flattened globular.

Height: Approximately 31.0 cm.

Plant spread: Approximately 61.5 cm.

Growth rate: Moderate to rapid.

Branching characteristics: No branches, fronds grow directly from the base.

Frond arrangement: Irregular, no pattern present.

Diameter of stem: No stems present.

FOLIAGE

Frond:

*Quantity per plant*.—Average 130.

*Frond type*.—Compound, pinnate.

*Pinnae per, frond*.—Average 56.

*Average frond length*.—Approximately 26.7 cm (excluding petiole).

*Average frond width*.—Approximately 8.1 cm.

*Average pinnae length*.—Approximately 4.3 cm.

*Average pinnae width*.—At base approximately 1.3 cm. At mid-section approximately 0.9 cm.

*Pinnae shape*.—Narrow deltoid to broad lanceolate.

*Pinnae apex*.—Obtuse.

*Pinnae base*.—Truncate.

*Overall frond shape*.—Narrow elliptic to lanceolate.

*Margin*.—Entire.

*Aspect*.—Slightly wavy, tip slightly curved downward.

*Texture of top surface*.—Smooth, moderately glossy.

*Texture of bottom surface*.—Smooth, slightly glossy.

*Color*.—Young foliage upper side: Yellow-green; near RHS 144A. Young foliage under side: Yellow-green; near RHS 144A. Mature foliage upper side: Green to Yellow-green; a color in between RHS 137B and 146A. Mature foliage under side: Green; near RHS 137B.

Venation:

*Type*.—Pinnate.

*Venation coloration upper side*.—Brown; near RHS N200A.

*Venation coloration under side*.—Brown; near RHS 200A.

Petiole:

*Length*.—Approximately 7.8 cm.

*Width*.—At geniculum: Approximately 0.15 cm. Above clump: Approximately 0.15 cm.

*Color*.—Upper side: proximal part Brown; near RHS N199B and 200D, middle part Yellow-green; RHS 152A, distal part slightly lighter; near RHS 152B and 152C. Under side: proximal part Yellow-green; near RHS 152B and 152C, middle and distal part Yellow-green; RHS 144A.

*Strength*.—Strong.

Pinnae petiole: No Pinnae petiole present.

Rachis description:

*Length*.—Approximately 25.9 cm.

*Width*.—Approximately 0.1 cm.

*Color*.—Upper side Yellow-green; near RHS 152D, lower side yellow-Green; near RHS 146C.

*Strength*.—Strong.

*Texture*.—Moderately glossy, sparsely covered with tufts of short soft hairs, average length 0.2 cm, coloured Grey-brown; near RHS 199A.

Other foliage characteristics: No.

OTHER CHARACTERISTICS

Spore production: No.

Temperature tolerance: Indoor fern, hardy to at least USDA zone 10.

Disease/pest resistance: Typical of *Nephrolepis exaltata*.

What is claimed is:

1. A new and distinct cultivar of *Nephrolepis exaltata* plant named 'Green Moment' as herein illustrated and described.

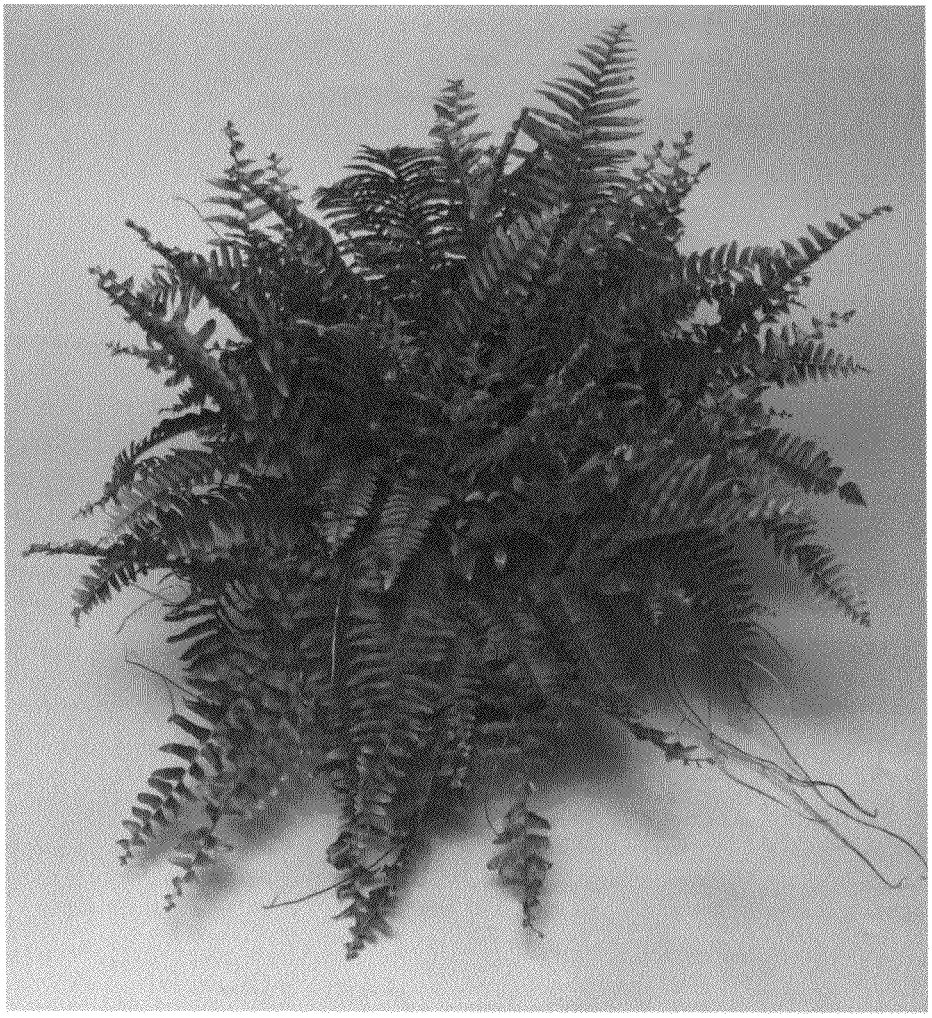

* * * * *